United States Patent
Kitahara et al.

(10) Patent No.: US 9,383,356 B2
(45) Date of Patent: Jul. 5, 2016

(54) LATEX PARTICLES FOR PARTICLE AGGLUTINATION ASSAY

(71) Applicant: SEKISUI MEDICAL CO., LTD., Tokyo (JP)

(72) Inventors: Shinichiro Kitahara, Tokyo (JP); Yuki Takahashi, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/431,555

(22) PCT Filed: Sep. 27, 2013

(86) PCT No.: PCT/JP2013/076389
§ 371 (c)(1),
(2) Date: Mar. 26, 2015

(87) PCT Pub. No.: WO2014/051098
PCT Pub. Date: Apr. 3, 2014

(65) Prior Publication Data
US 2015/0233906 A1   Aug. 20, 2015

(30) Foreign Application Priority Data

Sep. 27, 2012 (JP) ................................. 2012-213647

(51) Int. Cl.
*G01N 33/547* (2006.01)
*C08L 33/14* (2006.01)
*G01N 33/545* (2006.01)

(52) U.S. Cl.
CPC .............. *G01N 33/545* (2013.01); *C08L 33/14* (2013.01)

(58) Field of Classification Search
CPC .. G01N 33/545; G01N 33/546; G01N 33/547

USPC .................................................. 524/547, 577
See application file for complete search history.

(56) References Cited

U.S. PATENT DOCUMENTS 4,794,152 A   12/1988   Kobashi et al.
5,166,077 A   11/1992   Kihara et al.
(Continued)

FOREIGN PATENT DOCUMENTS

EP   1 314 982 A1   5/2003
EP   2 693 214 A1   2/2014
(Continued)

OTHER PUBLICATIONS

International Search Report, issued in PCT/JP2013/076389, dated Dec. 17, 2013.
(Continued)

*Primary Examiner* — Vu A Nguyen
(74) *Attorney, Agent, or Firm* — Birch, Stewart, Kolasch & Birch, LLP

(57) ABSTRACT

A particulate latex for high-sensitive agglutination assay that barely poses non-specific reactions and can readily prepare diagnostic reagents, and a reagent for agglutination assay including the particle are provided. A particulate latex for agglutination assay, including a first polymerizable monomer having a phenyl group, a second polymerizable monomer having a phenyl group and a salt of sulfonic acid, and a third polymerizable monomer represented by Formula (1):

$$CH_2=CR_1-COOCH_2CH_2O(PO_2)OCH_2CH_2-N(CH_3)_3 \quad (1)$$

where $R_1$ represents a hydrogen atom or a methyl group, wherein the density of functional groups in the third polymerizable monomer represented by Formula (1) on the surface of the particulate latex is 0.003 to 0.05 μmol/m².

6 Claims, 2 Drawing Sheets

(56) References Cited

U.S. PATENT DOCUMENTS

| | | | |
|---|---|---|---|
| 5,714,340 A | 2/1998 | Sutton et al. | |
| 7,166,476 B2* | 1/2007 | Shigenobu | C08F 220/60 435/7.1 |
| 7,279,339 B2* | 10/2007 | Sumida | G01N 33/54313 422/68.1 |
| 7,338,813 B2* | 3/2008 | Obana | C08F 212/08 428/403 |
| 7,368,252 B2* | 5/2008 | Sumida | C08F 30/02 435/7.2 |
| 7,867,785 B2 | 1/2011 | Obana | |
| 2003/0166302 A1 | 9/2003 | Shigenobu et al. | |
| 2004/0157276 A1 | 8/2004 | Sumida et al. | |
| 2004/0171176 A1 | 9/2004 | Obana | |
| 2005/0069967 A1 | 3/2005 | Sumida et al. | |
| 2006/0172351 A1 | 8/2006 | Sumida et al. | |
| 2008/0113452 A1 | 5/2008 | Obana | |

FOREIGN PATENT DOCUMENTS

| | | | |
|---|---|---|---|
| EP | 2 799 874 A1 | 11/2014 | |
| EP | 2 833 146 A1 | 2/2015 | |
| JP | 58-76762 A | 5/1983 | |
| JP | 58-34486 B2 | 7/1983 | |
| JP | 3-44085 B2 | 7/1991 | |
| JP | 6-265552 A | 9/1994 | |
| JP | 6-82128 B2 | 10/1994 | |
| JP | 8-10224 B2 | 1/1996 | |
| JP | 2002-318233 A | 10/2002 | |
| JP | 2002-365296 A | 12/2002 | |
| JP | 2003-231648 A | 8/2003 | |
| JP | 2005-106609 A | 4/2005 | |
| JP | 3708942 B2 | 10/2005 | |
| WO | WO 02/18953 A1 | 3/2002 | |
| WO | WO 03/005031 A1 | 1/2003 | |

OTHER PUBLICATIONS

English machine translation of JP-2002-318233-A, Oct. 31, 2002.
English machine translation of JP-2003-231648-A, Aug. 19, 2003.
English machine translation of JP-6-82128-B2, Oct. 19, 1994.
International Preliminary Report on Patentability and English translation of the Written Opinion of the International Searching Authority (Forms PCT/IB/338, PCT/IB/373 and PCT/ISA/237), Apr. 9, 2015, for International Application No. PCT/JP2013/076389.
Extended European Search Report, dated Apr. 4, 2016, for corresponding European Application No. 13842499.9.

* cited by examiner

LATEX PARTICLES FOR PARTICLE AGGLUTINATION ASSAY

TECHNICAL FIELD

The present invention relates to a latex particle (particulate latex) for high-sensitive agglutination assay, while highly suppressing a non-specific reaction. The present invention also relates to a reagent for agglutination assay using the particulate latex.

BACKGROUND ART

Immunoassays utilizing antigen-antibody reactions have been extensively performed to determine slight amounts of substances in samples in the field of clinical examination. Among these, latex immunoturbidimetry with particulate latices carrying antibodies (hereinafter also referred to as sensitized particulate latices) has been extensively used in laboratories because the latex immunoturbidimetry can be achieved by a simple operation for a short time. In latex immunoturbidimetry, the amount of an antigen or an antibody in a sample is determined through optical detection of a change in absorbance caused by agglutination of a sensitized particulate latex during formation of immune complexes. This change in absorbance is based on an apparent change in particle size caused by agglutination of the sensitized particulate latex.

As described in Patent Document 1, a polystyrene particulate latex mainly composed of polystyrene has been used in latex immunoturbidimetry because of ease in immobilization (sensitization) of antigens or antibodies specifically reactive with their target substances, relatively low cost, and easy control of the polymerization reaction of these particles. Regardless of such an advantage as physical adsorption (sensitization) of antigens or antibodies, the polystyrene particulate latex can also adsorb non-target proteins in samples. This adsorption of non-target proteins may cause so-called non-specific reactions, i.e., agglutination reactions of sensitized particulate latex not caused by a specific antigen-antibody reaction. The non-specific reactions should be prevented.

According to Patent Document 1, a particulate latex sensitized with an antigen or an antibody is blocked with bovine serum albumin (BSA) to prevent the non-specific reactions. Unfortunately, such blocking is still insufficient, and generates high background values. Accordingly, this measure has a severe challenge in preparing of reagents which enables highly sensitive measurement.

Patent Document 2 discloses preparation of polymer particles as carrier particles for diagnostic reagents. The polymer particles are prepared by aqueous copolymerization of styrene, a compound represented by the formula (101), and a salt of styrenesulfonic acid in the presence of a water-soluble radical polymerization initiator.

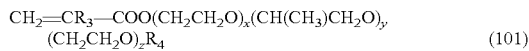
(101)

where $R_3$ represents H or $CH_3$; $R_4$ represents H or $CH_3$; x, y, and z each represent 0 or an integer of 100 or less and satisfy the relation $1 \leq x+y+z \leq 100$.

According to Patent Document 2, the resulting polymer particles pose less non-specific reaction. Unfortunately, such polymer particles containing a high content of compound represented by the formula (101) reduce a non-specific reaction, while barely adsorb antigens or antibodies physically onto their surfaces and cannot function as carrier particles for a diagnostic reagent. Furthermore, Patent Document 2 does not teach or suggest any compound for the preparation of the carrier particles except for styrene, the compound represented by the formula (101), the salt of styrenesulfonic acid, and the water-soluble radical polymerization initiator.

Patent Documents 3 and 4 each disclose an immunoassay reagent using as an agglutination accelerator a polymer containing as a main component monomer a compound represented by the formula (102):

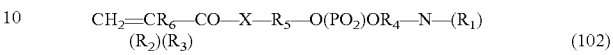
(102)

where $R_1$ to $R_3$ each independently represent a hydrogen atom or an alkyl group optionally having a hydroxyl group; $R_4$ represents an alkylene group; $R_5$ represents an alkylene group optionally having a substituent and/or an oxygen atom in the chain; $R_6$ represents a hydrogen atom or a methyl group; X represents an oxygen atom or an —NH— group.

According to these documents, the polymer may be a copolymer which preferably includes 20% or more structural units represented by the formula (102). The copolymer may contain a styrene derivative as a structural unit other than the structural unit represented by the formula (102). Unfortunately, these documents do not teach or suggest that the copolymer is present in a reaction solution as a linear polymer in a free state and is used in a form of a particulate latex.

According to Patent Document 4, addition of an agglutination accelerator, such as polyethylene glycol, to a reaction solution results in non-specific turbidity due to salting out to increase a blank value whereas such an agglutination accelerator including a polymer containing the compound represented by the formula (102) as a main-component monomer barely causes non-specific turbidity due to salting out. Unfortunately, Patent Document 4 does not teach or suggest that the polymer can prevent excess agglutination of dissociation samples that make non-specific agglutination reactions.

RELATED ART

Patent Document 1: Japanese Patent No. 3708942
Patent Document 2: Japanese Examined Patent Application Publication No. 58-34486
Patent Document 3: Japanese Unexamined Patent Application Publication No. 2005-106609
Patent Document 4: Japanese Unexamined Patent Application Publication No. 2002-365296

SUMMARY OF INVENTION

An object of the present invention, which has been made to solve the problems in the traditional latex immunoturbidimetry, is to provide a particulate latex for high-sensitive agglutination assay which enables high-sensitivity measurement, while highly suppressing a non-specific reaction, and also enables easy production of a diagnostic reagents, a reagent for agglutination assay which uses the particulate latex.

Solution to Problem

The present inventors, who have conducted extensive research to solve the problems, have found that the particulate latex for agglutination assay according to the present invention can be prepared by polymerizing a specific composition for the particulate latex, and have completed the present invention. The present invention is characterized by the following aspects:

Aspect [1]. A particulate latex for agglutination assay, including a first polymerizable monomer having a phenyl group, a second polymerizable monomer having a phenyl group and a salt of sulfonic acid, and a third polymerizable monomer represented by Formula (1):

$$CH_2=CR_1-COOCH_2CH_2O(PO_2)OCH_2CH_2-N(CH_3)_3 \quad (1)$$

where $R_1$ represents a hydrogen atom or a methyl group,
wherein the density of functional groups of the third polymerizable monomer represented by Formula (1) on the surface of the particulate latex is 0.003 to 0.05 μmol/m².

Aspect [2]. The particulate latex for agglutination assay according to Aspect [1], wherein the first polymerizable monomer having the phenyl group is at least one monomer selected from the group consisting of styrene, o-methylstyrene, p-methylstyrene, p-chlorostyrene, and 4-vinylbenzoic acid.

Aspect [3]. The particulate latex for agglutination assay according to Aspect [1] or [2], wherein the second polymerizable monomer having the phenyl group and the salt of sulfonic acid is at least one monomer selected from the group consisting of salts of styrenesulfonic acid, salts of divinylbenzenesulfonic acid, salts of o-methylstyrenesulfonic acid, and salts of p-methylstyrenesulfonic acid.

Aspect [4]. The particulate latex for agglutination assay according to Aspect [1], wherein the first polymerizable monomer having the phenyl group is styrene, and the second polymerizable monomer having the phenyl group and the salt of sulfonic acid is sodium styrenesulfonate.

Aspect [5]. The particulate latex for agglutination assay according to any one of Aspects [1] to [4], wherein the particulate latex carries an antigen or an antibody through physical adsorption.

Aspect [6]. A reagent for agglutination assay including the particulate latex for agglutination assay according to any one of Aspects [1] to [5].

Effects of Invention

The combination of the particulate latex for agglutination assay and the reagent for agglutination assay according to the present invention participates only in a target specific reaction (e.g., antigen-antibody reaction), which is an immune reaction involving a biologically derived substance, such as a protein, or a specific component in the assay reagent, while posing less non-target reaction unsuitable for the purpose of measurement (e.g., excess agglutination reactions occurring in dissociation samples), and thus can produce a diagnostic reagent that is more sensitive to distinctively measure specific agglutination reaction than traditional reagents. The particulate latex according to the present invention is prepared by a single-stage polymerization reaction, and is designed to be sensitized with an antigen or an antibody through physical adsorption. Accordingly, a high-sensitive particulate latex for agglutination assay can be prepared by a significantly simple process.

DESCRIPTION OF EMBODIMENT

Figure 1:
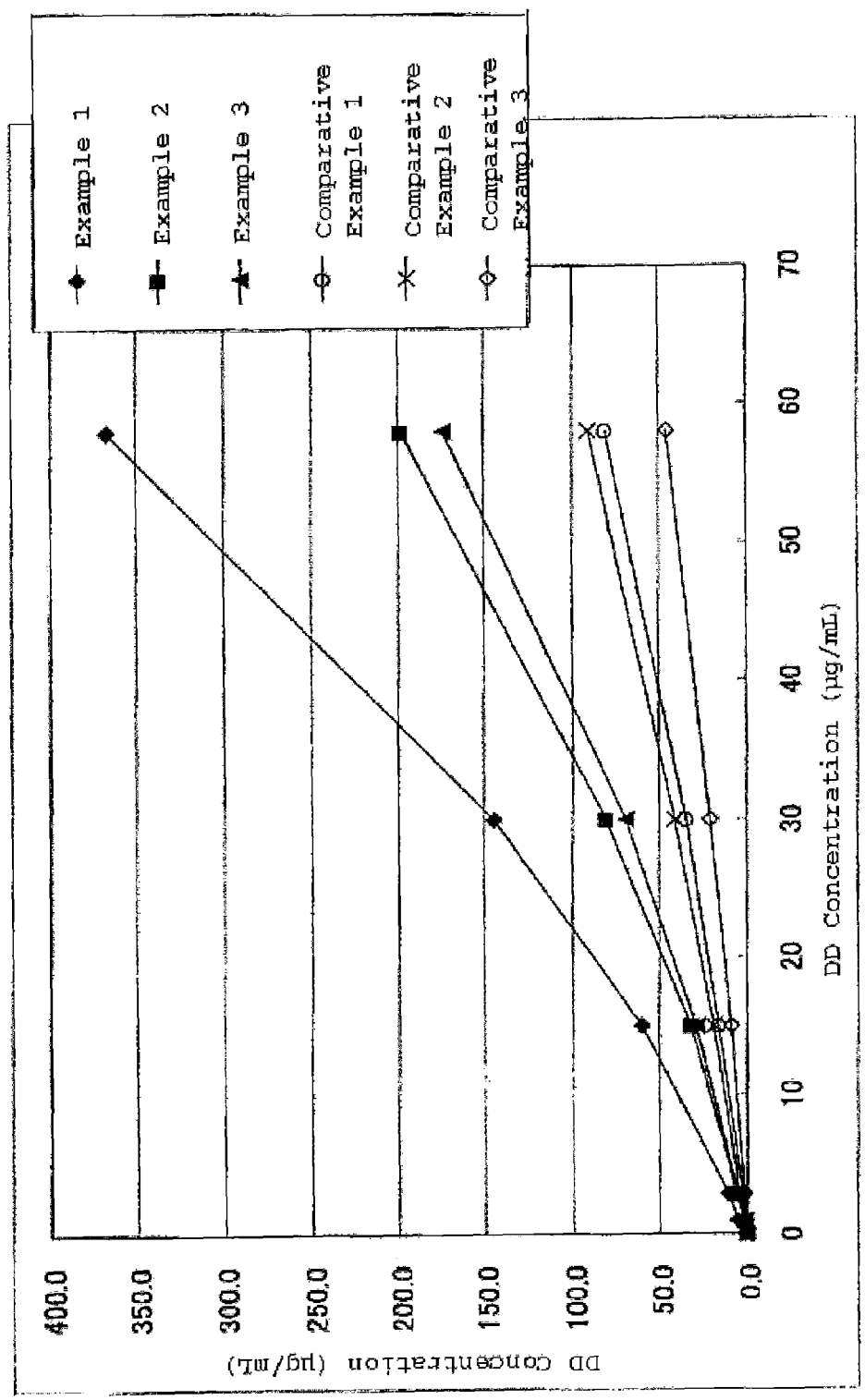
FIG. 1 is calibration curves produced by measurement of standard D-dimer antigens with particulate latices for agglutination assay sensitized with Anti-D-dimer antibody in Examples and Comparative Examples.

The present invention provides a particulate latex for agglutination assay including a first polymerizable monomer having a phenyl group, a second polymerizable monomer having a phenyl group and a salt of sulfonic acid, and a third monomer represented by Formula (1) (hereinafter referred to as "MPC monomer"), wherein the density of functional groups of the MPC monomer on the surface of the particulate latex is 0.003 to 0.05 μmol/m².

The present invention now will be described in more detail. Examples of the first polymerizable monomer having the phenyl group used in the present invention include, but should not be limited to, styrene, o-methylstyrene, p-methylstyrene, p-chlorostyrene, and 4-vinylbenzoic acid. These may be used alone or in combination. Among these, preferred is styrene.

The second polymerizable monomer having the phenyl group and the salt of sulfonic acid can be any monomer which enables a sulfonate group to be present on the surface of the particulate latex after polymerization. Examples of such monomers include salts of styrenesulfonic acid, salts of divinylbenzenesulfonic acid, salts of o-methylstyrenesulfonic acid, and salts of p-methylstyrenesulfonic acid. In the present invention, any sulfonic acid salt can be used. Examples thereof include sodium salts, potassium salts, lithium salts, and ammonium salts. These salts may be used alone or in combination. Among these, preferred are salts of styrenesulfonic acid, and more preferred is sodium styrenesulfonate.

The MPC monomer is represented by Formula (1):

$$CH_2=CR_1-COOCH_2CH_2O(PO_2)OCH_2CH_2-N(CH_3)_3 \quad (1)$$

where $R_1$ represents a hydrogen atom or a methyl group.

Specific examples thereof include 2-(acryloyloxy)ethyl-2-(trimethylammonium)ethyl phosphate where $R_1$ is a hydrogen atom), and 2-(methacryloyloxy)ethyl-2-(trimethylammonium)ethyl phosphate (where $R_1$ is a methyl group) (available from Tokyo Chemical Industry Co., Ltd.).

In the MPC monomer according to the present invention, the polar group has the same structure as that of the polar group of phospholipid that forms cell membranes. The polymer prepared through polymerization of the MPC monomer as a main component typically has the same characteristics as those of the components of a living cell membrane. The polymer can be artificially dissolved in water to form a bilayer membrane vesicle, so that the polymer can be stably present in water as a W/O/W emulsion. Utilizing such characteristics, applications of the polymer to drug delivery systems have been extensively studied. The polymer has high biocompatibility. Furthermore, the polymer applied onto plastic substrates barely adsorbs proteins in blood, therefore preventing non-specific adsorptions. For these characteristics, applications of the polymer to medical materials have been investigated. It is known that the polymer plays a role as an agglutination accelerator in applications to diagnostic reagents as described in Patent Documents 3 and 4. These applications, however, do not include applications of the polymer described in the present invention such that the polymer participates only in a target specific reaction (e.g., antigen-antibody reaction), which is an immune reaction involving a biologically derived substance, such as protein, or a specific component in an assay reagent, while posing less non-specific reaction unsuitable for the purpose of the measurement.

The particulate latex according to the present invention is prepared by soap-free emulsion polymerization in an aqueous medium containing the first polymerizable monomer having the phenyl group, the second polymerizable monomer having the phenyl group and the salt of sulfonic acid, and the MPC monomer. Such polymerization can be conducted by any known soap-free emulsion polymerization process. For example, the first polymerizable monomer having the phenyl group, the second polymerizable monomer having the phenyl group and the salt of sulfonic acid, the MPC monomer, and a polymerization initiator are added to water as a medium in a reaction container, and the reaction mixture is heated with stirring under a nitrogen atmosphere.

The polymerization temperature is preferably 50 to 100° C., more preferably 60 to 85° C. The polymerization time depends on conditions, such as the composition of the polymerizable monomers and the contents thereof, and the polymerization initiator, and is usually 5 to 50 hours.

A preferred aqueous medium is water (deionized water) alone or a mixed solvent of water and a water-miscible solvent. Examples of the mixed solvent include mixed solvents of water and alcohols, such as ethanol. Among these, preferred is water alone.

A known radical initiator can be used as the polymerization initiator. Examples thereof include persulfates, such as potassium persulfate, sodium persulfate, and ammonium persulfate; azo compounds, such as 2,2'-azobisisobutyronitrile, 2,2'-azobis(4-methoxy-2,4-dimethylvaleronitrile), and 2,2'-azobis-2,4-dimethylvaleronitrile; and organic peroxides, such as benzoyl peroxide, di-t-butyl peroxide, lauroyl peroxide, and t-butylperoxy-2-ethylhexanoate. Among these, preferred are persulfates, more preferred is potassium persulfate. The polymerization initiator can be used in any content. A preferred content of the polymerization initiator is in the range of 0.01 to 5 wt % relative to the polymerizable monomers.

Depending on applications of the particulate latex for agglutination assay according to the present invention, a polymerizable unsaturated monomer copolymerizable with the monomers described above may further be added during polymerization. Such a polymerizable unsaturated monomer can be any monomer typically used in radical polymerization. Examples thereof include (meth)acrylic acid, (meth)acrylate esters, styrene derivatives, (meth)acrylonitrile, (meth)acrylic acid amides, halogenated vinyls, vinyl esters, (meth)acrolein, maleic acid derivatives, and fumaric acid derivatives. Throughout the specification, the term (meth)acrylic acid indicates acrylic acid or methacrylic acid. The styrene derivatives indicate styrene derivatives other than the polymerizable monomer having the phenyl group and the polymerizable monomer having the phenyl group and the salt of sulfonic acid used in the present invention.

In the present invention, the MPC monomer can be used in any amount for polymerization such that the density of functional groups of the MPC monomer on the surface of the particulate latex is 0.003 to 0.05 µmol/m². A higher density of the functional groups on the surface of the particulate latex is not preferred regardless of its high effect of preventing non-specific reactions because such a higher density significantly reduces the sensitivity. A significantly low density of the functional groups on the surface of the particulate latex is not preferred because such a low density reduces the effect of preventing non-specific reactions by the MPC monomer and the resulting particulate latex is not superior to particulate latex not containing the MPC monomer. It is important to control the density of the functional groups of the MPC monomer to be 0.003 to 0.05 µmol/m², preferably 0.004 to 0.02 µmol/m² to prevent non-specific reactions without a reduction in sensitivity.

The density of the functional group of the MPC monomer is calculated from the following expression:

Density of functional groups (µmol/m²)=(molar amount of MPC monomer used in preparation of particulate latex)/(total surface area of prepared particulate latex).

The density of the functional group can be calculated by the following procedure:
Let r represent the average particle size (nm) of the prepared particulate latex,
Y represent the molar amount (µmol) of the MPC monomer used in preparation of the particulate latex, or $Y$=(weight (g) of MPC monomer used in preparation)/ (average molecular weight of the MPC monomer used in preparation), V represent the total volume (cm³) of the particulate latex,
S represent the total surface area (cm²) of the particulate latex,
x represent the total number of the particulate latex,
Z represent the density of the functional groups (µmol/m²), and
K represent the total weight (g) of the first polymerizable monomer having the phenyl group, the second polymerizable monomer having the phenyl group and the salt of sulfonic acid, the polymerization initiator, and the MPC monomer used in the polymerization reaction,
V and S are calculated as follows:

$$V=4/3\pi(r/2\times10^{-7})^3\times x, \text{ and}$$

$$S=4\pi(r/2\times10^{-7})^2\times x$$

lead to $S=6V/(r\times10^{-7})$;

then, $$Z = Y/(S \times 10^{-4})$$
$$= Y \times r \times 10^{-3}/6V;$$

where the specific gravity of polystyrene polymerized is 1.06 g/cm³, $$V=K/1.06, \text{ and}$$

$$Z=1.766\times10^{-4}\times Y\times r/K.$$

The average particle size of the particulate latex according to the present invention for agglutination assay is desirably 0.05 to 1.0 µm. An average particle size of less than 0.05 µm cannot attain sensitivity needed for measurement due to a significantly small amount of optical change caused by agglutination of the particulate latex, and increases the time for centrifugation during preparation of the reagent to increase cost of the reagent. With an average particle size of the particulate latex more than 1.0 µm and a high concentration of a target substance, the optical change caused by agglutination of the particulate latex exceeds the measurable range, and the measured amount of the optical change does not correspond to the amount of the target substance. The average particle size depends on the method and the apparatus used in the measurement using the particulate latex for agglutination assay. The average particle size is preferably 0.05 to 0.7 µm, more preferably 0.05 to 0.4 µm.

The coefficient of variation (CV value) in diameter of the particulate latex is preferably 20% or less. A coefficient of variation of more than 20% may cause low reproducibility between production lots during preparation of reagents, and thus reduce the reproductivity of the assay reagent. The coefficient of variation is more preferably 15% or less. The coefficient of variation in particle diameter is determined from the following equation:

Coefficient of variation in particle diameter (CV value)=(standard deviation of the particle diameters)/(average particle size).

The density of the functional groups, which represents the density of the MPC monomer on the surface of the particulate latex for agglutination assay according to the present invention, can be controlled by the molar amount of the MPC monomer used in preparation of the particulate latex. Namely, the amount of the functional groups on the surface of the particulate latex per unit area is specified in terms of the molar amount rather than the weight of the MPC monomer used in preparation of the particulate latex. The density of the functional groups can be determined by a simple operation from any MPC monomer having a different molecular weight as long as it can be represented by Formula (1):

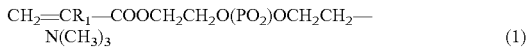
$$CH_2=CR_1—COOCH_2CH_2O(PO_2)OCH_2CH_2—N(CH_3)_3 \qquad (1)$$

where $R_1$ represents a hydrogen atom or a methyl group.

The particulate latex for agglutination assay according to the present invention is obtained in a state in which the particulate latex is suspended in water or an aqueous solvent. The particulate latex can be used in any content. The content is usually 1 to 20 wt %. At a content of less than 1 wt %, the reagent should be concentrated during preparation thereof. At a content of more than 20 wt %, the particulate latex may agglutinate.

Another aspect of the present invention provides a particulate latex for agglutination assay (reagent for agglutination assay) that carries a substance specifically bonding to a target substance through physical adsorption. The substance specifically bonding to a target substance can be any reagent for immunoserological tests (reagents used in immunological agglutination reactions and agglutination-inhibiting reactions) or any physiologically active substance typically used in biochemical assays. Among these, substances used in antigen-antibody reactions are suitable.

Examples of the substances used in antigen-antibody reactions include antigens or antibodies, such as proteins, nucleic acids, nucleoproteins, estrogen, and lipids. Examples of antigens include a variety of antigens, receptors, and enzymes, such as β2-microglobulin, C-reactive protein (CRP), insulin, human fibrinogen, ferritin, rheumatoid factors for testing rheumatoid arthritis (RA), α-fetoprotein (AFP), a mycoplasma antigen, and an HBs antigen. Examples of antibodies include a variety of antibodies against toxins and disease germs, such as an anti-streptolisyn O antibody, an anti-estrogen antibody, an anti-β2-microglobulin antibody, an anti-*Treponema pallidum* antibody, an antibody against syphilis lipid antigen, an anti-HBs antibody, an anti-HBc antibody, an anti-HBe antibody, an anti-PSA antibody, an anti-CRP antibody, an anti-insulin antibody, and an anti-D-dimer antibody. The antibodies can be immunoglobulin molecules themselves or fragments thereof, such as $F(ab')_2$. The antibodies to be used can be polyclonal antibodies or monoclonal antibodies.

A substance that specifically bonds to a target substance can be carried on (sensitized to) the particulate latex by any known process as long as the immobilization or the sensitization is carried out through physical adsorption.

The substance carried on the particulate latex can be optionally blocked with bovine serum albumin and be dispersed in an appropriate buffer to prepare a dispersion of a sensitized latex. The dispersion of a sensitized latex, a buffer, and a standard substance to be used in measurement can be used as a kit of reagents for agglutination assay.

The substance specifically reactive with a target substance can be carried on the particulate latex in any amount. The amount depends on the type of the substance specifically reactive with a target substance.

For use of an assay reagent including the particulate latex for agglutination assay carrying an antigen or an antibody, the reagent can contain a variety of sensitizers to enhance the sensitivity for assay and promote an antigen-antibody reaction. Examples of the sensitizers include alkylated polysaccharides, such as methyl cellulose and ethyl cellulose; pullulan; and polyvinylpyrrolidone.

The particulate latex according to the present invention can highly prevent the non-specific reaction. Furthermore, the particulate latex may contain proteins, such as albumin (bovine serum albumin, ovalbumin), casein, and gelatin, and decomposed products thereof, amino acid, or a surfactant to prevent the non-specific reaction caused by other substances existing in samples or to enhance the stability of the reagent.

The target substance may be diluted with an appropriate diluent. The diluent can be any buffer at a pH of 5.0 to 9.0. Examples thereof include phosphate buffers, glycine buffers, tris buffers, borate buffers, and citrate buffers.

The assay reagent including the particulate latex for agglutination assay according to the present invention carrying an antigen or an antibody can determine the amount of the reacted target substance in a sample by optical measurement of the degree of agglutination of the particulate latex caused by the specific reaction of the target substance in the sample with the substance reactive with the target substance carried on the particulate latex. The optical measurement can be conducted with any one of standard biochemical automatic analyzers, such as optical detectors that can detect the intensity of scattered light, the intensity of transmitted light, and the absorbance, or any optical apparatus provided with these detectors in combination.

The degree of agglutination can be optically determined by any known method. Examples thereof include turbidimetry that detects agglutination as an increase in turbidity, a method that detects agglutination as a change in particle size distribution or average particle size, and a method that detects integrating sphere turbidity in which a change in forward-scattered light caused by agglutination is measured with an integrating sphere, and then compared with the intensity of transmitted light.

Examples of the method of measuring the change in the degree of agglutination also include rate assays in which at least two values are obtained from measurement at different times, and the degree of agglutination is determined based on an increase between these two values measured at different times (a rate of increase); and end point assays in which one value is obtained from measurement at one time (typically a time considered as the end point of the reaction), and the degree of agglutination is determined from the obtained value. Among these, end point assays according to turbidimetry are suitable because the operation is simple and speedy.

EXAMPLES

The present invention will now be described in more detail by way of Examples. The particle sizes of the latices for agglutination assay prepared in Examples were each measured as follows.

Measurement of Particle Size of Latex for Agglutination Assay:

The particulate latex for agglutination assay was put onto a collodion film by a normal method. Images of particles were photographed with a transmission electron microscope, and the particle diameters (of 100 or more particles) on the images were measured to determine the average particle size and the standard deviation.

Example 1

Ultrapure water (1000 g), a styrene monomer (135 g), 2-(methacryloyloxy)ethyl-2-(trimethylammonium)ethyl phosphate (available from Tokyo Chemical Industry Co., Ltd.) (0.021 g), sodium styrenesulfonate (1.2 g), and potassium persulfate (0.7 g) were placed in a glass reactor (volume: 2 L) provided with a stirrer, a refluxing cooler, a thermodetector, a nitrogen inlet pipe, and a jacket. After the container was purged with nitrogen gas, the mixed solution was subjected to polymerization for 24 hours at 70° C. with stirring at 210 rpm. After the polymerization was terminated, the solution was filtered through a filter paper to extract a particulate latex. The particulate latex was dialyzed through a dialyzing membrane for 48 hours to purify the particulate latex. The particulate latex had a particle size of 0.108 µm (CV: 9.7%) and an MPC density of 0.010 µmol/m$^2$.

Example 2

A particulate latex was prepared as in Example 1 except that the amount of 2-(methacryloyloxy)ethyl-2-(trimethylammonium)ethyl phosphate (available from Tokyo Chemical Industry Co., Ltd.) (0.021 g) was 0.009 g. The particulate latex had a particle size of 0.102 µm (CV: 10.4%) and an MPC density of 0.004 µmol/m$^2$.

Example 3

A particulate latex was prepared as in Example 1 except that the amount of 2-(methacryloyloxy)ethyl-2-(trimethylammonium)ethyl phosphate (available from Tokyo Chemical Industry Co., Ltd.) (0.021 g) was 0.042 g. The particulate latex had a particle size of 0.105 µm (CV: 10.1%) and an MPC density of 0.019 µmol/m$^2$.

Comparative Example 1

A particulate latex was prepared as in Example 1 except that 2-(methacryloyloxy)ethyl-2-(trimethylammonium)ethyl phosphate (available from Tokyo Chemical Industry Co., Ltd.) (0.021 g) was not used. The particulate latex had a particle size of 0.107 µm (CV: 10.3%). Since the MPC monomer was not used, the MPC density was 0.

Comparative Example 2

A particulate latex was prepared as in Example 1 except that the amount of 2-(methacryloyloxy)ethyl-2-(trimethylammonium)ethyl phosphate (available from Tokyo Chemical Industry Co., Ltd.) (0.021 g) was 0.005 g. The particulate latex had a particle size of 0.105 µm (CV: 9.8%) and an MPC density of 0.002 µmol/m$^2$.

Comparative Example 3

A particulate latex was prepared as in Example 1 except that the amount of 2-(methacryloyloxy)ethyl-2-(trimethylammonium)ethyl phosphate (available from Tokyo Chemical Industry Co., Ltd.) (0.021 g) was 0.120 g. The particulate latex had a particle size of 0.110 µm (CV: 9.1%) and an MPC density of 0.058 µmol/m$^2$.

[Application]

A D-dimer reagent for agglutination assay was evaluated with the particulate latices prepared in Examples and Comparative Examples. The following reagent and materials were used.

<Reagent and Materials>

Anti-D-dimer antibody

Buffer for preparing a particulate latex carrying an antibody: 20 mM Tris-HCl (pH: 8.0) was used.

Buffer for blocking used was 2% (w/v) BSA in 20 mM Tris-HCl (pH: 8.0).

Buffer for diluting a sample used was 0.15% (w/v) BSA in 30 mM Tris-HCl (pH: 8.5).

<Preparation of D-Dimer Reagent for Agglutination Assay>

After the particulate latices prepared in Examples 1 to 3 and Comparative Examples 1 to 3 were each purified by centrifugation, the particulate latices were each diluted to 5% (w/v) with Buffer for preparing a particulate latex carrying an antibody to prepare a diluted latex solution.

Anti-D-dimer antibody was diluted to 1 mg/mL with Buffer for preparing a particulate latex carrying an antibody to prepare a diluted antibody solution.

The diluted antibody solution (1 volume) was added to the diluted latex solution (1 volume) while the diluted latex solution was being stirred. The mixed solution was further stirred. Buffer for blocking (2 volumes) was further added, and the mixed solution was continuously stirred. The solution was recovered to prepare a D-dimer reagent for agglutination assay. The D-dimer reagent was adjusted to 0.5% (w/v) with a buffer to prepare a dispersion of an antibody-sensitized latex. D-dimer antigen standard solutions were measured with the dispersion of an antibody-sensitized latex to produce a calibration curve.

Apparatus: Hitachi 7170 automatic analyzer

Wavelength: 570/800 nm

Operating temperature: 37° C.

Target substance (0 to 58 µg/mL D-dimer standard solution): 12 µL

First reagent (Buffer for diluting a sample): 30 mM Tris-HCl (pH: 8.5) containing 0.15% (w/v) BSA: 100 µL Second reagent (dispersion of 0.5% (w/v) antibody-sensitized particulate latex): 100 µL Points for measurement: 18-34

[Measurement 1]

Measurement was performed with the antibody-sensitized particulate latices (0.5% (w/v)) sensitized with Anti-D-dimer antibody in Examples 1 to 3 and Comparative Examples 1 to 3 according to the method described above to produce calibration curves (FIG. 1). FIG. 1 evidently shows that the antibody-sensitized particulate latices in Examples 1 to 3 enable relatively high-sensitive assay. FIG. 1 also shows that the antibody-sensitized particulate latices in Comparative Examples 1 to 3 are less sensitive than the antibody-sensitized particulate latices in Examples.

[Measurement 2]

Figure 2:
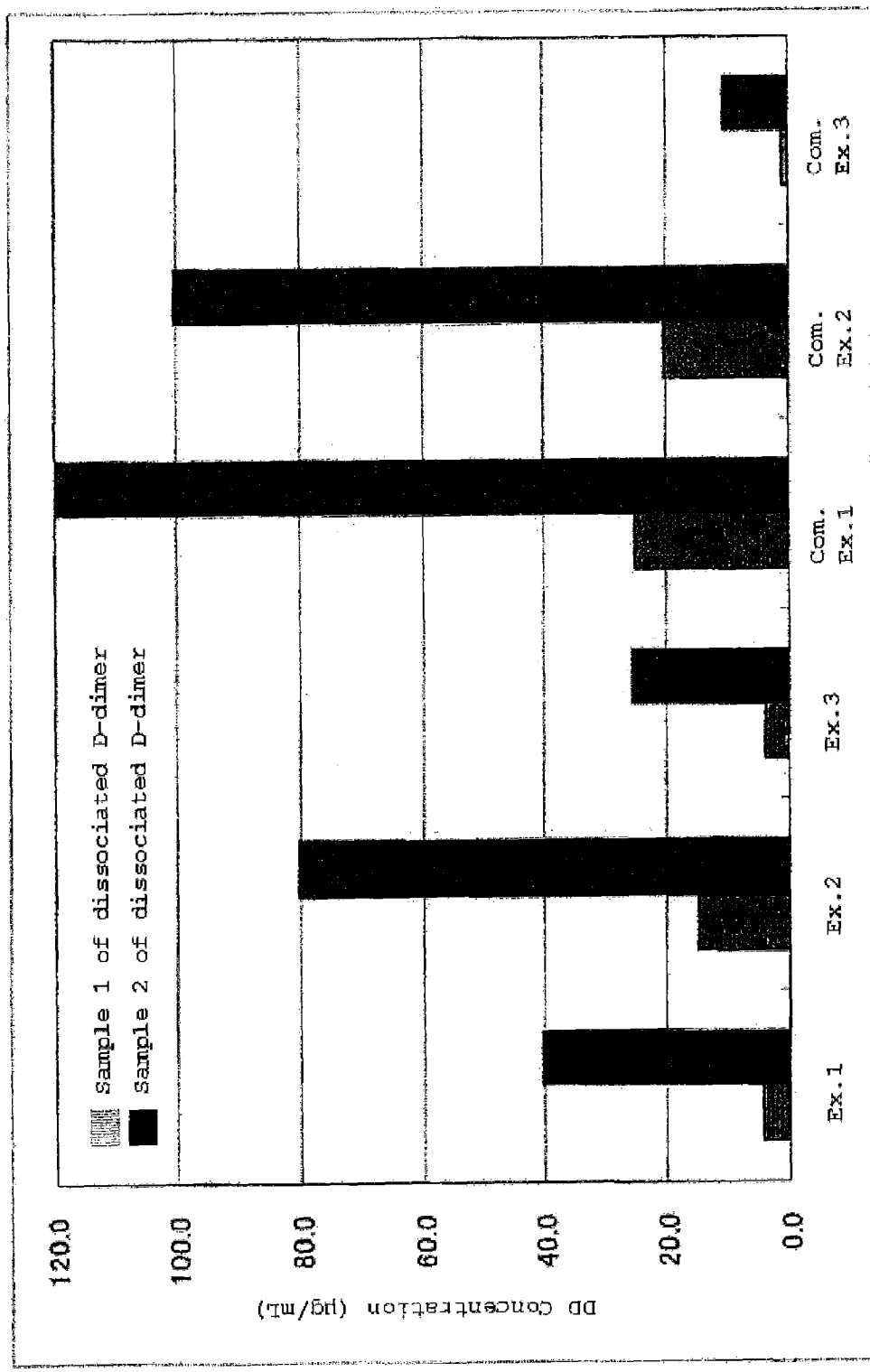
FIG. 2 is a graph showing the concentrations of D-dimers in D-dimer dissociation Samples 1 and 2 determined with the particulate latex for agglutination assay sensitized with Anti-D-dimer antibody according to Examples and Comparative Examples, the concentrations being converted with the calibration curves in FIG. 1.

Antibody-sensitized particulate latices (0.5% (w/v)) in Examples 1 to 3 and Comparative Examples 1 to 3 sensitized with Anti-D-dimer antibody and two D-dimer dissociation Samples were subjected to the measurement according to the method described above, and the observed values were converted into the concentrations of the D-dimers with the calibration curves produced in Measurement 1. The D-dimer dissociation sample refers to a sample in which a non-specific agglutination reaction was observed in a system measured by the traditional immunoturbidimetry of the D-dimer. The results are shown in FIG. 2. FIG. 2 evidently shows that the antibody-sensitized particulate latices in Examples 1 to 3 more significantly prevent the non-specific agglutination reactions in D-dimer dissociation Samples than the particulate latex in Comparative Example 1 not containing the MPC monomer does. FIG. 2 also shows that the antibody-sensitized particulate latex in Comparative Example 3 equally prevents the non-specific agglutination reactions in D-dimer dissociation Samples as the antibody-sensitized particulate latices in Examples 1 to 3 do, whereas the sensitivity is significantly reduced as shown in Measurement 1. The reason is probably because a significantly high density of the MPC monomer prevents the surface of the particulate latex from sufficiently adsorbing (being sensitized with) the antibody.

INDUSTRIAL APPLICABILITY

The particulate latex for agglutination assay together with the reagent for agglutination assay, according to the present invention, can cause only the target specific agglutination reaction without adsorbing non-target proteins in samples which cause the non-specific agglutination reactions. Accordingly, the particulate latex for agglutination assay and the reagent for agglutination assay according to the present invention can provide a diagnostic reagent more sensitive than traditional reagents. The particulate latex for agglutination assay and the reagent for agglutination assay according to the present invention are useful as reagents for immunoserological tests (reagents used in immunological agglutination reactions and agglutination-inhibiting reactions) and reagents for testing physiologically active substances typically used in biochemical assays.

The invention claimed is:

1. A particulate latex for agglutination assay, comprising:
a first polymerizable monomer having a phenyl group;
a second polymerizable monomer having a phenyl group and a salt of sulfonic acid; and
a third polymerizable monomer represented by Formula (1):

$$CH_2=CR_1-COOCH_2CH_2O(PO_2)OCH_2CH_2-N(CH_3)_3 \quad (1)$$

where $R_1$ represents a hydrogen atom or a methyl group, wherein the density of functional groups of the third polymerizable monomer represented by Formula (1) on the surface of the particulate latex is 0.003 to 0.05 μmol/m².

2. The particulate latex for agglutination assay according to claim 1, wherein the first polymerizable monomer having the phenyl group is at least one monomer selected from the group consisting of styrene, o-methylstyrene, p-methylstyrene, p-chlorostyrene, and 4-vinylbenzoic acid.

3. The particulate latex for agglutination assay according to claim 1 or 2, wherein the second polymerizable monomer having the phenyl group and the salt of sulfonic acid is at least one monomer selected from the group consisting of salts of styrenesulfonic acid, salts of divinylbenzene sulfonic acid, salts of o-methylstyrenesulfonic acid, and salts of p-methylstyrenesulfonic acid.

4. The particulate latex for agglutination assay according to claim 1, wherein the first polymerizable monomer having the phenyl group is styrene, and the second polymerizable monomer having the phenyl group and the salt of sulfonic acid is sodium styrenesulfonate.

5. The particulate latex for agglutination assay according to claim 1, wherein the particulate latex carries an antigen or an antibody through physical adsorption.

6. A reagent for agglutination assay comprising the particulate latex for agglutination assay according to claim 1.

* * * * *